United States Patent

Rupp et al.

[11] Patent Number: 5,826,696
[45] Date of Patent: Oct. 27, 1998

[54] APPARATUS FOR SEPARATING SMALL ARTICLES

[75] Inventors: Michael Rupp, Pforzheim; Werner Schiffer, München; Gyula Varhaniovsky, Pfinztal; Thomas Kirchner, Karlsruhe; Nikolaus Asteriadis, Baltmannsweiler, all of Germany

[73] Assignee: Walter Grassle GmbH, Pfinztal-Sollingen, Germany

[21] Appl. No.: 513,238

[22] Filed: Aug. 10, 1995

[30] Foreign Application Priority Data

Aug. 11, 1994 [DE] Germany ............... 44 28 452.7
Mar. 31, 1995 [DE] Germany ............... 195 11 948.7

[51] Int. Cl.⁶ .................................. B65G 29/00
[52] U.S. Cl. ................ 198/392; 198/396; 198/397; 198/443
[58] Field of Search .................. 198/392, 396, 198/397, 443

[56] References Cited

U.S. PATENT DOCUMENTS

| | | | |
|---|---|---|---|
| 1,455,639 | 5/1923 | McGinnis . | |
| 2,892,567 | 6/1959 | Smith et al. . | |
| 3,613,861 | 10/1971 | Whitecar . | |
| 3,817,423 | 6/1974 | McKnight | 198/33 |
| 3,942,645 | 3/1976 | Aronson | 198/271 |
| 4,306,649 | 12/1981 | Berge . | |
| 4,632,028 | 12/1986 | Ackley | 198/384 |
| 4,673,077 | 6/1987 | Taniguchi . | |
| 4,757,382 | 7/1988 | Kaziura et al. | 198/689 |

FOREIGN PATENT DOCUMENTS

| | | |
|---|---|---|
| 0615931 A2 | 9/1994 | European Pat. Off. . |
| 959359 | 3/1957 | Germany . |
| 1163239 | 2/1961 | Germany . |
| 2031031 | 1/1971 | Germany . |
| 2403619 C2 | 8/1974 | Germany . |
| 24 53 699 | 5/1975 | Germany ............... 198/392 |
| 3608398 A1 | 10/1986 | Germany . |
| 3820540 A1 | 12/1989 | Germany . |
| 2-231307 | 9/1990 | Japan . |
| 729223 | 5/1955 | United Kingdom . |
| 1552843 | 9/1979 | United Kingdom . |

*Primary Examiner*—William E. Terrell
*Assistant Examiner*—Khoi H. Tran
*Attorney, Agent, or Firm*—Antonelli, Terry, Stout & Kraus, LLP.

[57] ABSTRACT

In an apparatus for inspecting small articles, such as in particular tablets, for obtaining a precise lining up of the articles there is a rotationally symmetrical separating body (4) rotatable about a vertical rotation axis (A), which has a substantially conical feed section (6) and a section (7, 8) for orienting and/or separating the articles (G) surrounded by a ring slot (S) at least corresponding to the thickness of the articles (G). The separating section (8) is subdivided into individual shafts (11) for receiving the articles (G) by ribs (9) circumferentially succeeding one another with a spacing at least corresponding to the width or diameter of the articles (G).

25 Claims, 9 Drawing Sheets

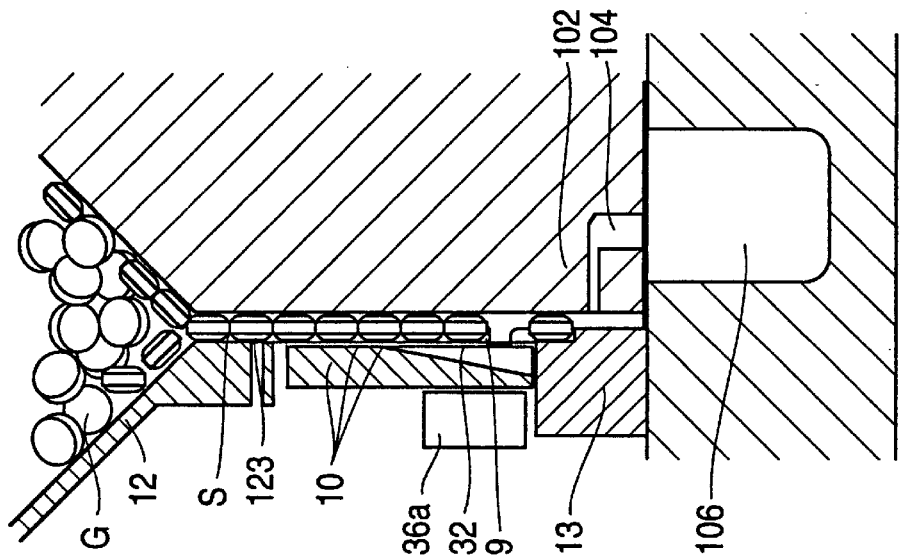
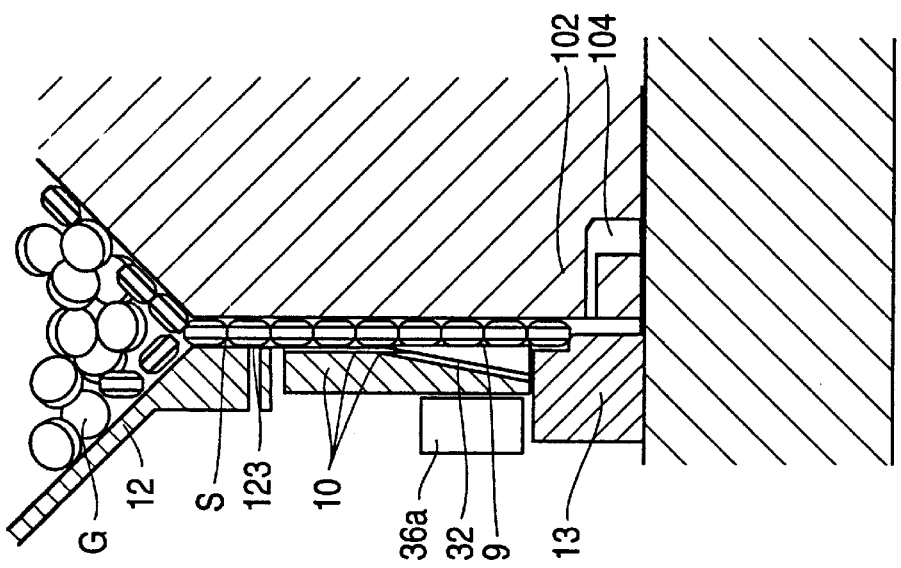
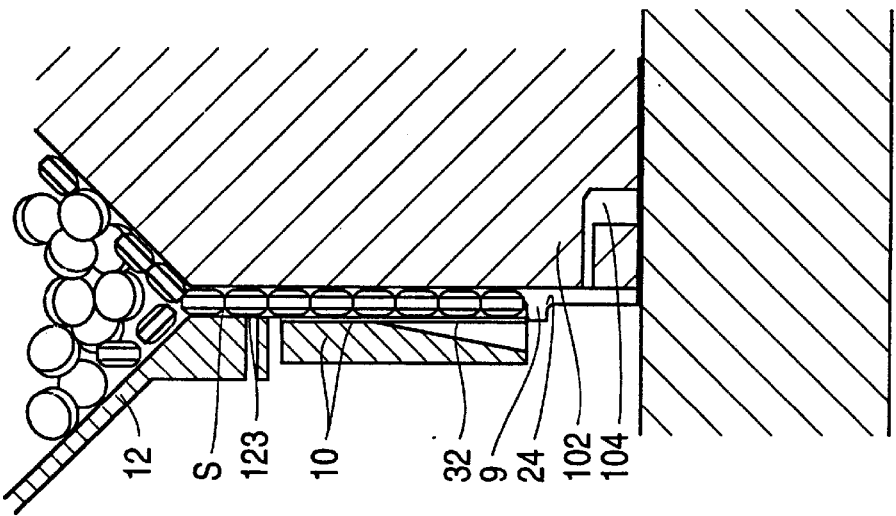

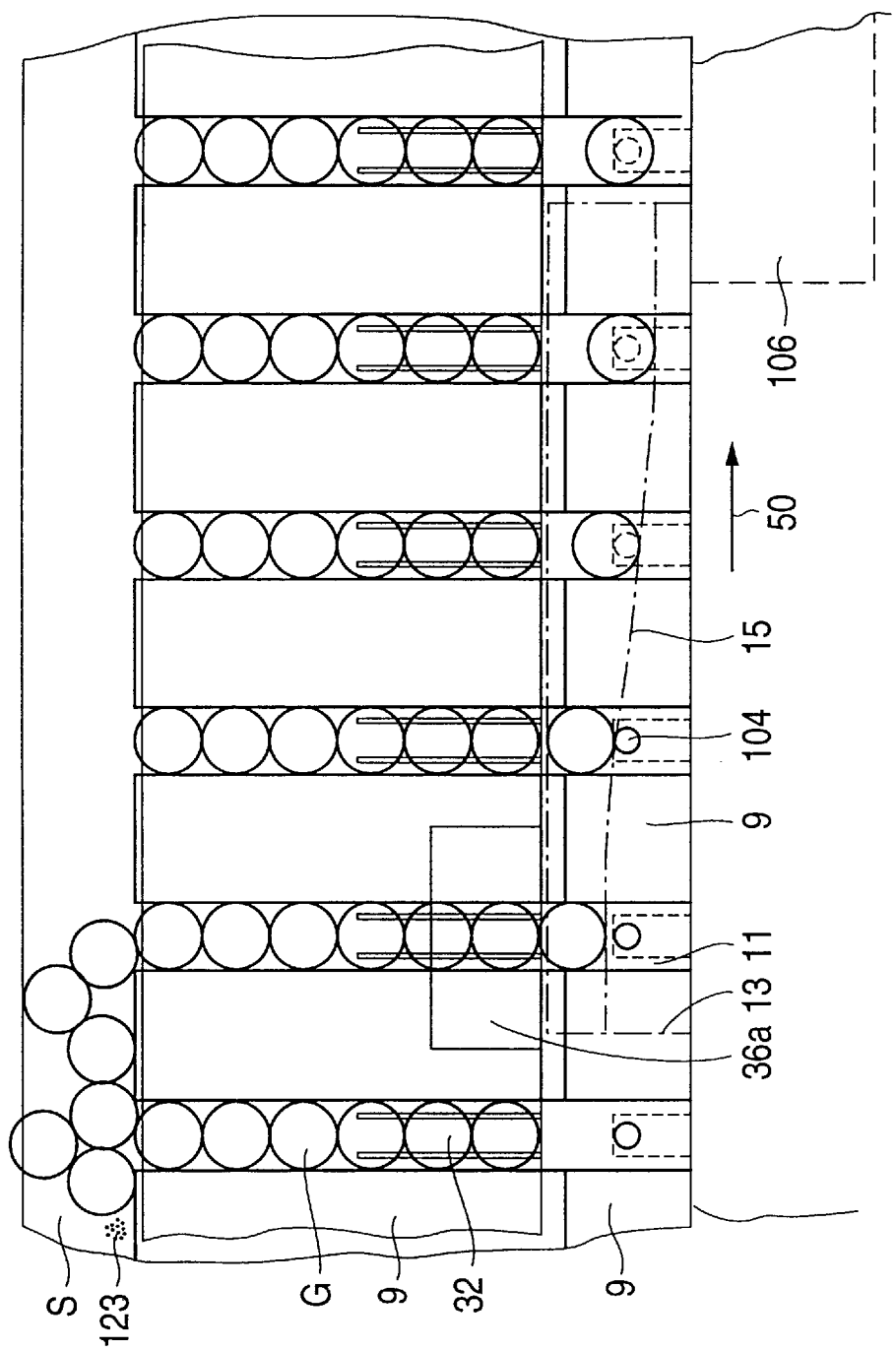

APPARATUS FOR SEPARATING SMALL ARTICLES

FIELD OF THE INVENTION

The invention relates to an apparatus for separating or individualizing small articles such as tablets, dragees, film tablets, capsules, etc.

BACKGROUND OF THE INVENTION

1. Description of the Prior Art

Small articles must to be examined or inspected to an increasing extent for defects. The small articles can be tablets, dragees, film tablets, capsules, etc., small batteries, as well as rice grains and in the latter case e.g. the black grains are to be removed.

In particular tablets and the like must be inspected to an increased extent for defects, because e.g. in the case of damage to a tablet the ingestion of such a damaged tablet would lead to a dose or active constituent proportion change for the patient. Film tablets or dragees are provided with a coating, so that the body is only supplied in delayed form with the active constituents contained therein. However, if the coating is damaged or at least partly absent, then there are changes to the characteristics and/or action of the ingested medicament, which must be avoided.

In order that the articles can be inspected or individually further processed, they must not only be separated, but also supplied to an inspection or further processing means in precisely defined positions and in particular in precisely defined intervals.

German patent 36 08 398 discloses an apparatus for separating small articles, which has a hopper or funnel, a vibrating feeding device located below it and having a vibrator, a vibrating chute connected thereto, as well as a tablet sorting mechanism. The latter comprises a driven rotary table with a fixed circumferential wall in sliding contact with the outer edge of the rotary table. A fixed pin extends through the center of the rotary table and around it are located a plurality of orientation guides. On the edge of the circumferential wall of the rotary table are provided a thickness and a width gate for the articles to be separated. The articles arrive on the rotary table via the vibrating feeding device and as a result of the action of the table and the orientation guides are to be successively oriented in a single row along the circumferential wall of the rotary table. They are sorted regarding thickness by the thickness gate and regarding width by the width gate. From the width gate the articles then arrive on a belt conveyor, which passes them on to an apparatus for their inspection. It is a disadvantage of this apparatus that between the articles to be conveyed it is impossible to prevent an irregular spacing, so that there are empty zones when supplying a testing device. In addition, such an apparatus is only usable for circular articles. In the case of articles with a non-circular profile the separating apparatus must be in each case replaced by another suitable apparatus.

The problem according to the invention is therefore to provide an apparatus for separating small articles, such as in particular tablets, dragees, film tablets, capsules, etc., in which it is possible to achieve a separation and a precise orientation and alignment of the articles and having a high throughput.

SUMMARY OF THE INVENTION

According to the invention the problems of the prior art are solved by an apparatus of the aforementioned type through a rotationally symmetrical separating body rotatable about a vertical rotation axis and which has a substantially conical feed section and a section for orienting and/or separating the articles surrounded by a ring slot at least corresponding to the thickness of the articles, the separating section being subdivided into individual shafts for receiving the articles by circumferentially spaced ribs having a spacing at least corresponding to the width or diameter of the articles.

The apparatus according to the invention leads to a sure and reliable separation of the articles.

In the shafts initially it is possible to intermediately store several articles. The shafts form a magazine. This ensures that at the outer end of a shaft there is always an article ready for delivery and no idling occurs.

Due to the fact that several shafts are juxtaposed over the circumference in the separating section, the individual articles during their orientation do not have to be exclusively successively lined up and instead the parallel shafts allow a parallel processing, which permits a high throughput despite the limited rotary speed of the separating body. The latter is appropriate, so that the articles, particularly if they are of a sensitive nature, are not crushed during orientation and separation, which would otherwise in particular be the case if a torus surrounding the separating body and leading to the ring slot has a fixed construction, i.e. did not rotate together with the separating body.

In order to improve the orientation in the case of a high article throughput, in a variant the torus is constructed in a funnel-shaped manner in the vicinity of the feed section.

According to a particularly preferred development the orientation section of a first embodiment has a cylindrical construction. Thus, the articles to be separated drop into the ring slot solely under the influence of gravity, without transverse forces acting thereon, which could also lead to damage and as a result blockages and accumulations are avoided. In a second embodiment a separating section serving the same function has a cylindrical construction. Alternatively, when connected to the orientation section, the separating section has a substantially frustum-shaped construction, so that a transfer area following onto the separating section is provided for a substantially horizontal delivery of the articles.

In order to obtain a precise relative spacing of the separated articles, according to a further development of the first embodiment at least one disk is provided, which in one end face has suction holes subject to vacuum action on a circular path for retaining the articles. In this construction, according to a further preferred embodiment, ribs are constructed on the separating body and the suction holes in the transfer area of the separating body move synchronously with the ends of the shafts. In the case of a synchronous drive the lower end of a shaft in the delivery area thereof at a delivery position is always associated with a suction hole or is aligned therewith, so that the article is transferred in a positionally accurate manner to the suction hole and can be suctioned through the latter. Although fundamentally the diameter of the suction disk could be the same as the separating section in its transfer area, according to a preferred development the disk diameter is larger than that of the separating body in the transfer area. As a result the articles retained by the suction holes on the disk are kept away and therefore free from the separating body, so that they can be supplied to examination devices located on the disk circumference or to a further transfer. Fundamentally the ends of the shafts and the suction holes can in each case have different circumferential spacings, if they are guided in a synchronously timed, superimposed manner solely in the transfer area. However, according to a preferred development the shafts and the suction holes have the same circumferential spacing. The term synchronous movement then means that the suction holes and the ends of the shafts have the same circumferential speed (although having different angular speeds in the case of a different radial spacing from their rotation axis).

According to a further development of the second embodiment a support is provided with substantially coaxially positioned circumferential surfaces holding the articles by vacuum on the support. For this purpose the separating section is preferably arranged in a concentrically synchronous manner to the support and is firmly connected thereto. The articles are consequently secured at precisely defined positions of the circumferential wall of the support and can then be inspected for defects by means of suitable detecting devices. For this purpose, according to a preferred development, there is a detector device positioned radially to a first support and facing the same and the movement path of the suction holes holding the articles on the support. Due to the fact that the articles are held in precisely defined suction holes on the support, they can also be delivered in a precisely defined position, a tested or inspected article and the test result associated therewith always remaining associatable with one another. Such a support can easily be fixed to its drive by means of screw connections, so that it is also easily replaceable. Due to the fact that the articles are held on circumferential walls of the support, the vacuum exerted acts in opposition to the centrifugal forces acting on the articles. The suction force consequently needs to only overcome the centrifugal forces.

In order to be able to inspect the entire surface of the articles, the invention provides a further support with suction holes arranged on a circular path in a circumferential wall, the circumferential walls of the support moving synchronously past, but in opposite directions to one another with a spacing slightly exceeding the thickness of the articles, the suction holes face one another and at a transfer point where the circumferential surfaces of the two supports are oriented parallel to one another, are oriented in a aligned manner to one another. In order to assist the transfer of articles from one support to another or the positioning on the first support, the suction holes of the support are connectable to stationary suction channels. In the first support the suction hole is only connected to the associated stationary suction channel for producing the vacuum following the positioning of the articles. The transfer of the articles from one support to the other takes place during simultaneous support action by means of centrifugal force in that the suction holes of the first support leave the area of the associated stationary suction channel, i.e. the suction action is eliminated here, whereas the suction holes of the second support reach the area of the associated suction channel and consequently a suction action occurs in the direction of the second support. In this way the articles are suctioned with one area on the suction holes of the further support and this area precisely faces the area with which they were directed towards the suction holes of the first support, so that it is now also free and can be optically inspected.

According to a preferred development, in the vicinity of the movement path of the suction holes detector devices are provided, whereof one is oriented radially to the support and faces the latter, whereas at least one further device is oriented axially parallel and faces the movement path of the suction holes. Thus, the lateral faces of the articles can also be optically inspected.

According to a further development of the invention a device is provided for transferring the articles to the separating body and in particular said device transfers at the conical feed section of the separating body. The supply device is preferably constructed as a supply chute. To avoid fragments of the articles to be inspected from reaching the testing disk or support, where they would block the suction holes, which would reduce the throughput, according to a further development the device for transferring the articles has a screen or sieve for separating the fragments. Complete articles slide over the correspondingly adapted screen, whereas fragments of articles drop through the screen meshes.

In order that the articles do not pass in an uncontrolled manner to the separating body in the area upstream of the suction holes, there are preferably unlockable hold back members for closing the grooves or shafts in the downwards direction. The hold back members are preferably lamellar springs, which can be unlocked by magnets. By means of a preferably provided bypassing means with a support curve the articles, following the unlocking of the lamellar springs, are supplied in a positionally accurate manner when using supports to the suction hole of the first support.

Alternatively, the bottom article is held by a holding device switchable for releasing the article and the holding device has a raisable spring holding the bottom article. Through a parallel arrangement of several shafts, whereof one always delivers an article in the transfer area, even in the case of a high throughput it is possible to allow the springs to operate in a low frequency manner, which permits their use and therefore a very precise transfer of the articles to the suction holes.

An essential feature of the apparatus according to the invention is that all the parts are individual parts, which can be easily replaced. If following the inspection of one type of article, a different type of article has to be inspected, it is merely necessary to replace the individual parts of the apparatus, which can be rapidly carried out. The previously used parts can be cleaned, without this holding up for a long period the further use of the apparatus which can consequently cause long idle times. This is particularly important with tablets, because on the conveying elements not even the smallest residues thereof must be left behind, if different tablet types having different active ingredients are to be separated by the apparatus, because such residues of the previously tested tablets, e.g. in dust form, can contaminate the subsequently tested tablets.

BRIEF DESCRIPTION OF THE DRAWINGS

Further advantages and features of the invention can be gathered from the following description, which relates to two embodiments of the invention, with reference to the attached drawings, wherein show:

FIG. 9 is a section through the separating area of the apparatus prior to separation.

FIG. 10 is a section through a separating area during separation.

FIG. 11 is a section through the separating area after separation.

FIG. 12 is a development of the support in the separating area.

DESCRIPTION OF THE PREFERRED EMBODIMENTS

Figure 1:
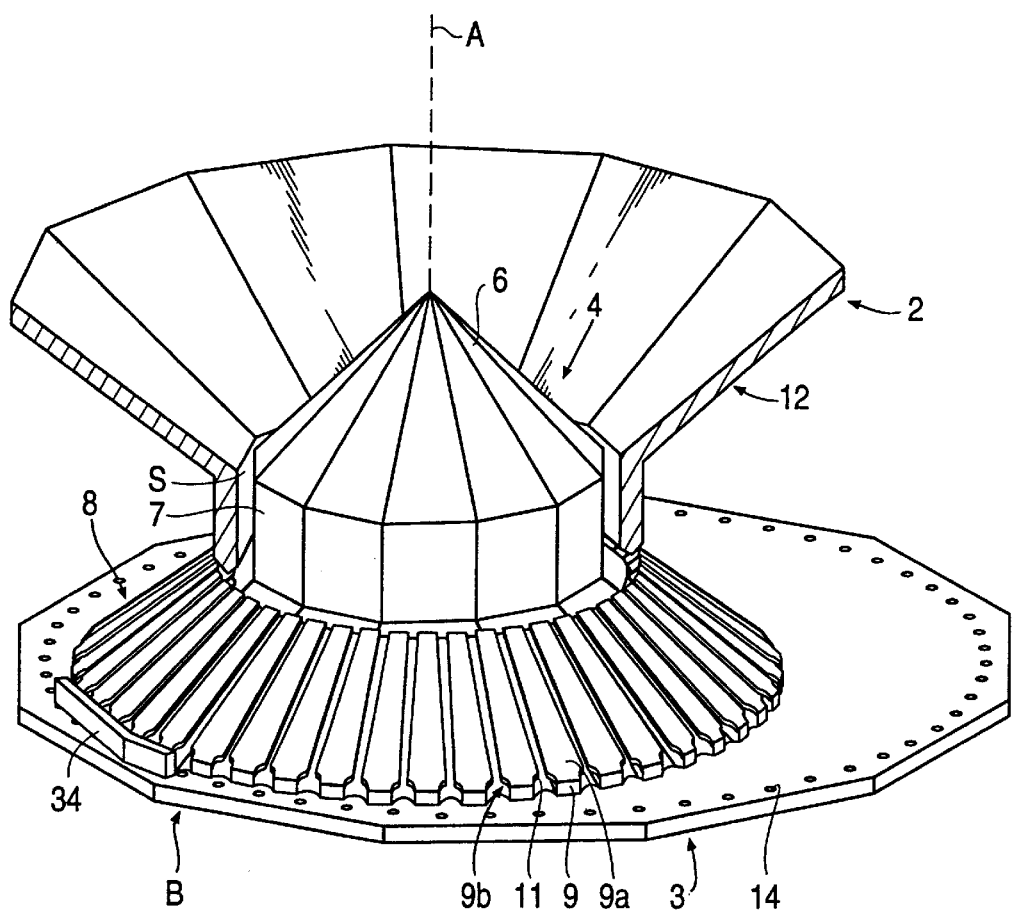
FIG. 1 is a perspective view of a first embodiment of the apparatus according to the invention with broken away areas.
Figure 2:
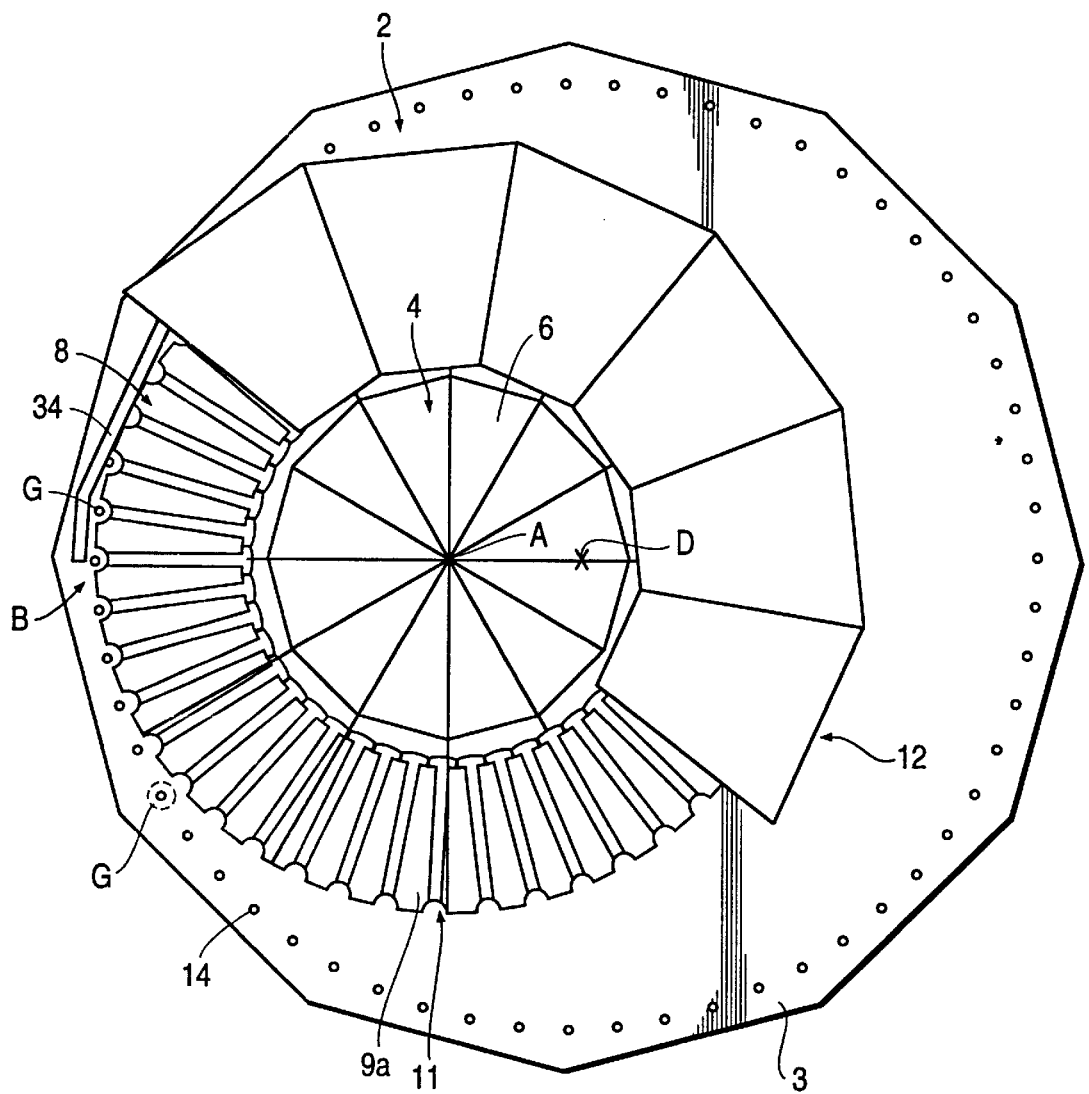
FIG. 2 is a plan view of the apparatus of FIG. 1.
Figure 3:
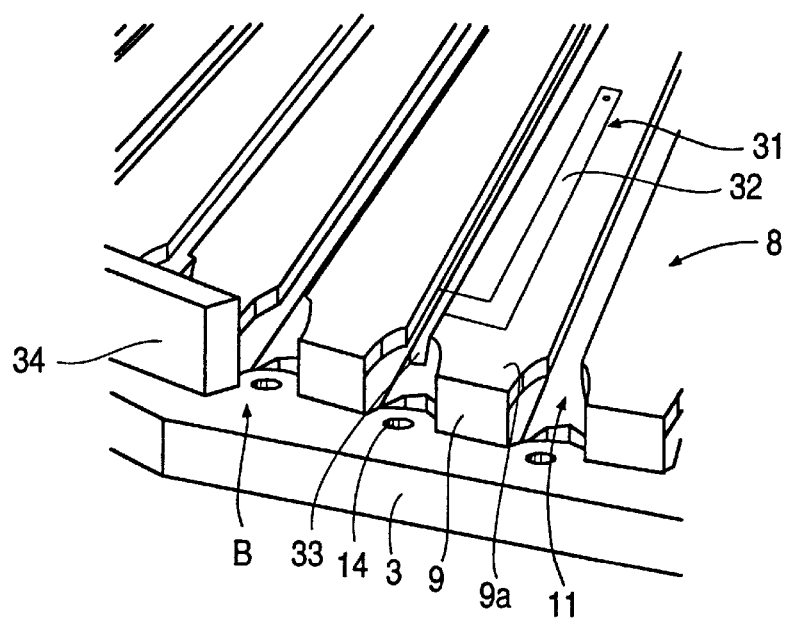
FIG. 3 is a larger scale detail view of FIG. 1 with a holding device for the articles.
Figure 4:
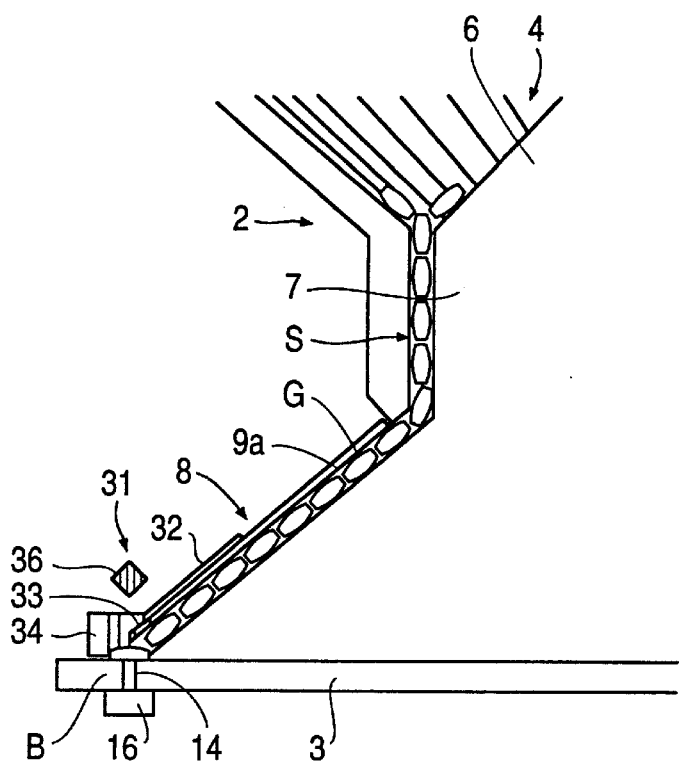
FIG. 4 is a vertical section through part of the apparatus of FIG. 1.
Figure 5:
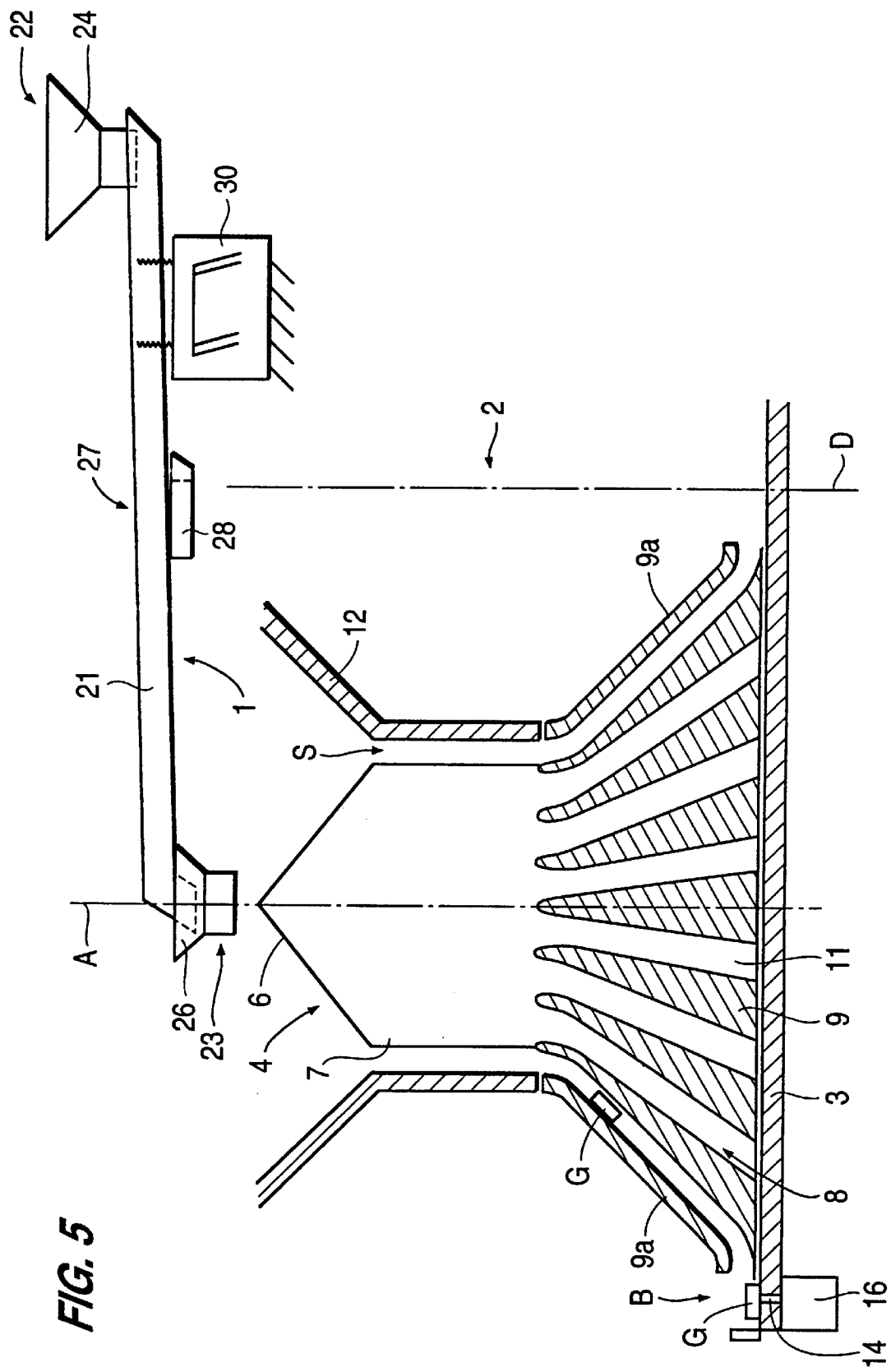
FIG. 5 is a highly diagrammatic side view with broken away areas of an apparatus according to the invention and a supply device.

In the drawings the same components are given the same reference numerals.

The first embodiment of the apparatus according to the invention for separating or individualizing small articles, such as tablets and the like, shown in FIGS. 1 to 6 has a supply device 1 (FIGS. 5/6), a separating device 2 and a reception disk 3.

The separating device 2 has a rotationally symmetrical separating body 4, which is rotatable about its axis of symmetry A and rotates during operation of the apparatus. The separating body 4 has an upper, substantially conical feed section 6, to which is connected a substantially cylindrical orienting section 7, to which is connected in the lower area a substantially conically widening separating section 8, which forms magazines. It is provided with T-ribs 9, between which are formed undercut shafts 11 of constant width, the "crossbar" 9a of the T partly covering the shafts 11. The separating body 4 is surrounded by a stationary torus 12, which is funnel shaped in the area surrounding the feed section 6. In the orienting section 7 it surrounds the separating body 4 with a finite, constant radial spacing, so that between the orienting section 7 and the torus 12 is formed a slot S, whose width substantially corresponds to the thickness of the articles to be separated. The width of the shafts 11 corresponds to the width of the articles to be separated. The height of the shafts 11 below the "crossbar" 9a corresponds to that of the slot S.

Due to the fact that the crossbars 9a on the circumferential edge have a break 9b, the articles G, such as tablets, etc., can be delivered horizontally onto the disk 3, which is provided in the delivery area B of the separating body 4 and namely in the marginal area thereof suction holes 14, which are connected to a circular suction channel 16. Therefore the articles delivered by the separating device 2 to the disk 3 are firmly suctioned onto the latter through the suction holes 14 by means of the suction channel 16. The circumferential spacing of the suction holes 14 following along the edge of the disk 3 corresponds to the circumferential spacing of the shafts 11 in the delivery area B, so that the articles G are always delivered by a shaft exactly at a suction hole 14.

The bottom article G, such as a tablet, is held or retained by a holding device 31 (FIG. 3) with a leaf spring 32, which is in each case fixed to a crossbar 9a of the ribs 9 and resiliently, i.e. in frictionally engaging manner rests on the article by a nose or projection 33. In addition, a wall 34 is provided round a partial circumferential of the lower edge of the separating section 8 of the separating device 2 and extends up to the transfer area B, in that it has a distance from the ends of the ribs 9 or shafts 11 corresponding to the width of the articles G and preventing said articles from sliding outwards. The spring 32 can be raised by an electromagnet 36 (FIG. 4) for freeing the articles in the transfer area.

The supply device 1 (FIGS. 5/6) is provided for supplying the articles G to be separated and has a supply chute 21, which is constructed as a vibrating chute. From a feed point 22 it passes in slightly inclined manner to a transfer area 23, which is located somewhat over the centre of the separating body 4, which is defined by its rotation axis A. In the feed area 22 is provided a funnel or hopper 24, into which can be fed the articles to be tested such as tablets, either from a feed line leading to the funnel, or from containers such as bags or sacks. There is also a hopper or funnel 26 for transferring the articles to the disk 3 in the transfer area 23.

In an intermediate area of the chute 21 is provided a wide-mesh screen or sieve 27 (particularly FIG. 6), whose mesh width is such that it does not permit the passage of undamaged articles and instead permits the further conveying thereof to the hopper 26, whereas fragments smaller than the articles to be tested drop through the screen 27. Below the screen 27 is provided a continuation channel 28 by means of which the fragments are disposed of. The chute 21 is given vibratory movements by a vibrating drive 30.

As in the represented embodiment, the disk 3 generally has a larger diameter than the separating device 2, so that the rotation axis D of the disk 3 does not coincide with the rotation axis A of the separating body 4.

The suction channel 16 is connected to a vacuum pump (not illustrated).

The articles G to be inspected in the embodiment according to FIGS. 1 to 6 are delivered by means of the reception hopper 24 and drop from the latter into the vibrating chute 21, which is vibrated by the vibrating drive 30. As a result of this and gravity the articles are moved along the chute 21 and slide over the screen 27, through which drop fragments, which can be then disposed of via the channel 28. The articles to be tested drop through the hopper into the central area of the conical feed section 6 of the separating body 4 and slide on the cone up to the inlet of the slot S, being so oriented by the rotary movement that they rest flat on the cone 6, i.e. with the height thereof perpendicular to the face of the cone 6, so that in this way they can slide into the slot S. In the latter they accumulate in the oriented sense and are individually received by shafts 11, in which they follow one another in a line. If during the rotation of the separating body 4 one of the shafts 11 enters the transfer area B, then the spring 32 is raised by the magnet 36, so that the projection 33 of the spring 32 frees the bottom article, which slides out of the corresponding shaft 11 and is immediately sucked by means of the suction hole 14 onto the disk 3. The spring 32 drops away again and holds the following article G in the particular shaft. During the further movement of the separating body 4 and the disk 3 the following shaft 11 moves and in the same way the next suction hole 14 into the transfer area B, so that the first article G of the following shaft 11 can be transferred to said following suction hole 14 and so on.

The articles G are located on the disk 3 in separated, clearly spaced succession and can be reliably further processed. They can be inspected, particularly optically, or transferred in clearly defined manner to further devices.

Figure 7:
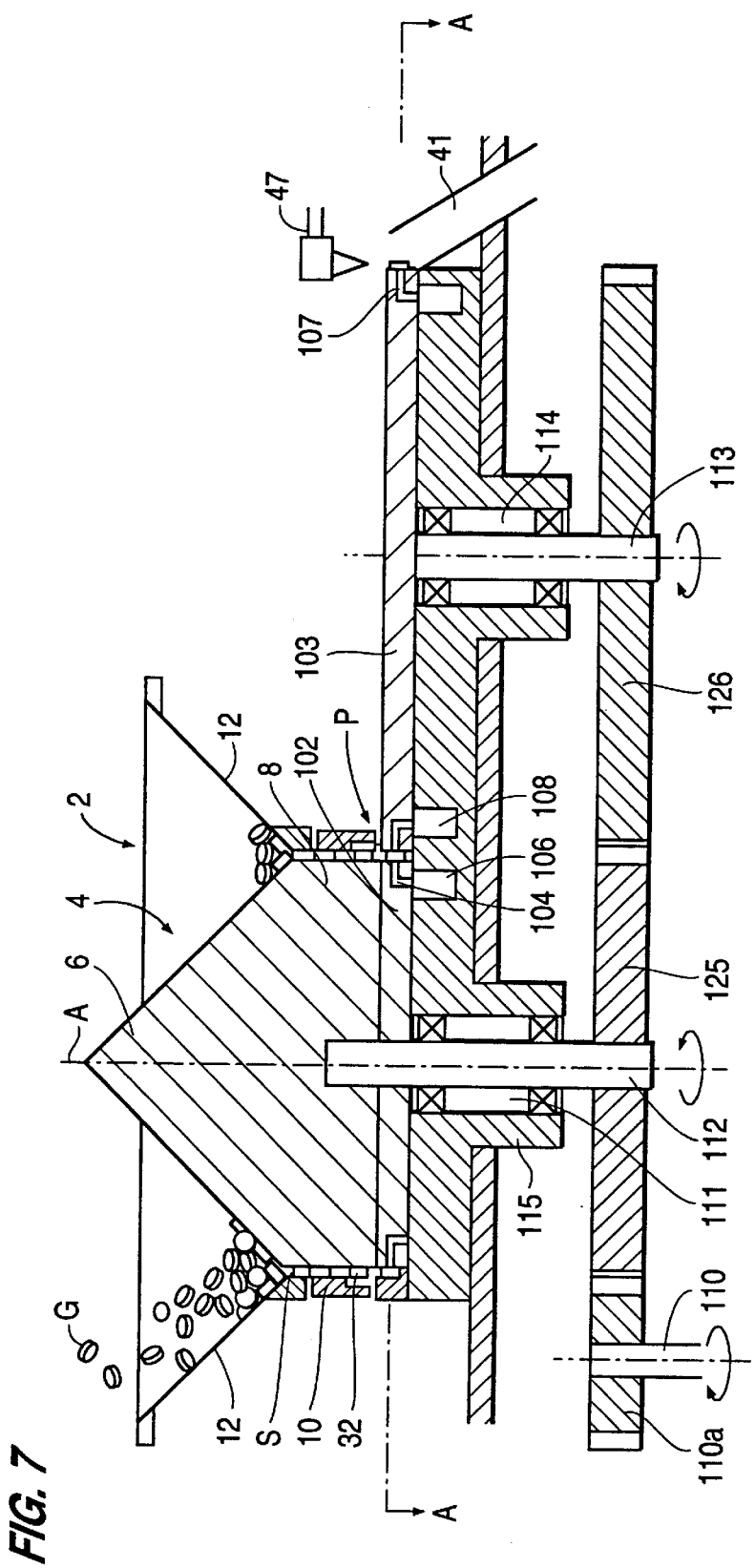
FIG. 7 is a diagrammatic vertical section through a second preferred embodiment of the apparatus according to the invention corresponding to B—B in FIG. 8 with the following inspection device.

The second embodiment of the apparatus according to the invention, shown in FIG. 7, has a separating device 2 for the articles G to be tested, such as tablets and the like, as well as a testing or inspecting device P. The separating device 2 has a rotationally symmetrical separating body 4, which is rotatable about the axis of symmetry A and is rotated during the operation of the apparatus. The separating body 4 has an upper, substantially conical feed section 6, to which is connected a substantially cylindrical separating section 8, which forms magazines.

In particular in the vicinity of its feed section 6, the separating body 4 is surrounded by a torus 12 in the form of a hopper. As from the transition area from the feed section 6 to the separating area 8 between the latter and the lower area of the torus 12 is formed a ring slot S, which has a slightly greater thickness than that of the articles G to be tested.

At the separating section 8 in a lower area below the ring slot S (FIG. 12) webs or ribs 9 are formed, between which are formed grooves or shafts 11, whose width slightly exceeds the width of the articles G or the diameter thereof. The bottom of the grooves or shafts 11 is aligned with the face of the cylindrical separating section 8 in the vicinity of the slot S. In the radial direction the grooves or shafts 11 are closed by a circular cover 10 firmly connected to the separating body 4 or its separating section 8. In the upwards direction towards the ring slot S, the grooves or shafts 11 are open, whereas in the downwards direction they are closed by lamellar springs 32. The cover 10 ends in the lower area at the same height as the springs 32. Below the springs 32 the radial height of the webs 11 is reduced to approximately half the thickness of the articles G. In the lower area the separating body 4 and in particular its separating section 8 is constructed as a support 102 for the articles G or is firmly connected to such a support 102.

Over a partial circumference of the support 102 are provided stationary magnets 36a, which act in contactless manner on the lamellar springs 32 moved past and which have on their underside a horizontal bend and consequently raise them to such an extent that the grooves or shafts 11 are freed at the bottom and an article G can slide through downwards. The springs 32 are supported on the cover 10.

In the same area as the magnets 36a a bypass means 30 is provided in stationary manner and has a support curve 15, which extends radially roughly up to half the thickness of the articles G. When the spring 32 is open the curve 15 allows an article G to slide in the groove initially to completely below the spring 32. The curve 15 is lowered to such an extent that a separated article G comes to rest concentrically or centrally in front of a suction hole 104.

The support 102 for the articles G together with the separating body 4 is located on a shaft 112, which is mounted in a pivot bearing 111 in a stationary machine part 115. The shaft 112 is also connected in non-rotary manner to a toothed disk 125, which has the same diameter as the support 102 and is driven by means of a pinion 110a connected to a driving shaft 110 by a not shown drive.

In the stationary machine part 115 a suction channel 16 is formed over a partial circumference. In the outer circumferential wall of the support 102 are formed suction holes 104, which can be brought by means of a suction channel into fluid connection with the suction channel 106 in the stationary machine part 115.

Alongside the support 102 is provided a second support 103 in the form of a circular disk, which also has in its circumferential walls suction holes 107, which are connected by means of suction channels to a suction channel 108 in the stationary machine part 115. The support 103 by means of a shaft 113, which is mounted by means of a bearing 114 in the stationary machine part 115, can be driven by a toothed disk 126, whose diameter corresponds to the support 103 and which meshes with the toothed disk 125. The channels 106, 108 are connected to at least one, not shown vacuum pump.

As a result of the synchronous drive of both supports 102, 103 by means of the meshing toothed disks 125, 126 with opposite rotation direction connected to the shafts 112, 113, the supports 102, 103 in a transfer point 105 have the same circumferential speed and the same movement direction. The supports 102, 103 are so connected by the shafts 112, 113 that the suction holes 104, 107 in the transfer point 105 are guided in precisely aligned manner, so that there the articles G to be tested can be transferred without any relative position change from one support 102 to the other support 103. For transfer purposes the suction holes 104 in the transfer area 105 leave the area of the stationary suction channel 106, so that the suction action for the support 102 is eliminated. At the transfer point 105 the suction holes 107 reach the area of the stationary suction channel 108, so that as from this transfer point 105 the suction action for the support 103 is produced.

Figure 8:
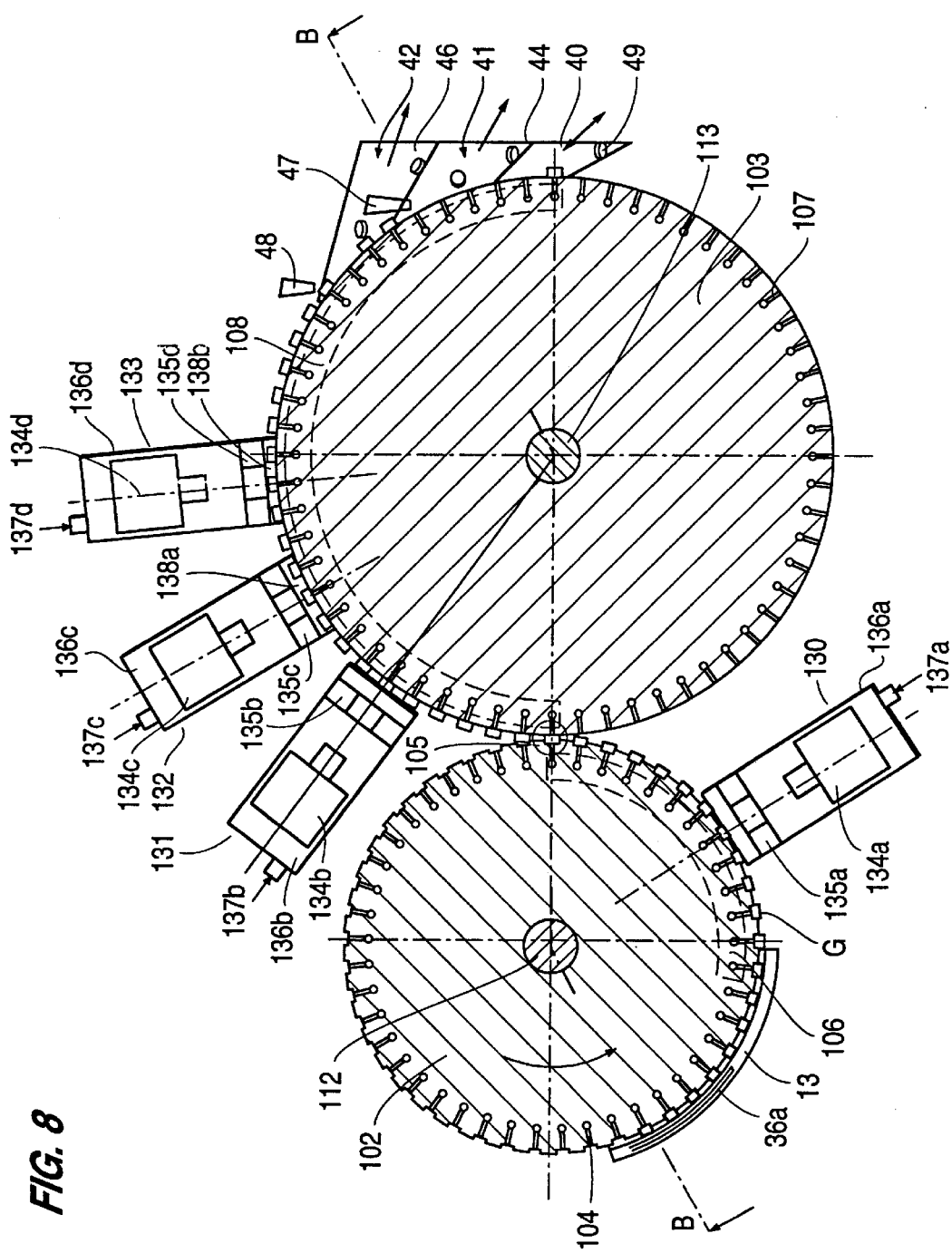
FIG. 8 is a diagrammatic cross-section through the apparatus along A—A in FIG. 7.

Alongside the support 102 is provided a stationary camera system 130. Camera systems 131, 132, 133 are positioned on the circumference of the support 103. The camera systems 131–133 can be positioned alongside, above and below the path traversed by the suction holes 17 of the support 103 (FIG. 8). The camera systems 130 to 133 are connected to image processing units (not illustrated). A camera system 130–133 in each case has a casing 136a–d with a lighting device 135a–d, as well as a camera 134a–d, in particular a video surface camera. In the represented embodiment the camera systems 132, 133 are also provided with mirrors 138a and b for observing the circumferential faces of the articles G.

In order to avoid any impairing of the image quality and a faulty testing or inspection of the articles due to the entry of dust into the air space between the lens of the camera 134a–d and the articles and consequently keep the air space free from dust, filtered air is supplied to the casings 136a–d and said air can pass out of the casings in the direction of the articles G.

The lighting devices 135a–d can be equipped with a plurality of light emitting diodes having different wavelengths and the diodes having the same wavelength can be separately controlled in a groupwise manner. However, it is also possible to provide the lighting devices 135a–d which in each case only emit light of the same wavelength, so that the lighting devices 135a–d can be simply replaced as a complete unit for illumination with a different wavelength.

The camera systems 136a–d used for the optical testing and inspection processes are connected by means of a connection 137a–d to an image evaluation unit (not illustrated), by means of which the images or pictures taken by the camera 134a–d can be evaluated. The image evaluation unit is designed in such a way that there is an evaluation of the gradients of the grey value change of adjacent image points. This makes it possible to detect breaks, varnish damage, as well as displacements, particularly in the case of multicoating tablets, and in particular the smallest surface defects, so that the articles suffering from these problems can be eliminated.

For this purpose below the support 103 in the circumferential direction behind the camera systems 131–133 are provided distributing devices 40, 41, 42 in the form of distributing chutes. The pass-out devices 41, 42 have continuation channels 44, 46 for the articles G, as well as ejecting devices in the form of blast nozzles 47, 48 with which the articles G can be separated from the support 103 by an air jet, so that they drop into one of the continuation channels 44, 46. Thus, the blast nozzle 48 ejects the defective articles G into the channel 46, whereas the blast nozzle 47 ejects the satisfactory articles G into the continuation channel 44. The distributing device 40 is only provided with a continuation channel 9. As the suction channel 108 terminates at the start of the continuation channel 49, all articles not ejected for some reason by one of the ejecting devices 47, 48 as a result of the elimination of the vacuum at the suction holes 107 automatically drop into the continuation channel 49 and are disposed of as defective articles. As a result of this measure it is very reliably insured that only satisfactory articles G pass into the channel 44 and are further processed.

Figure 6:
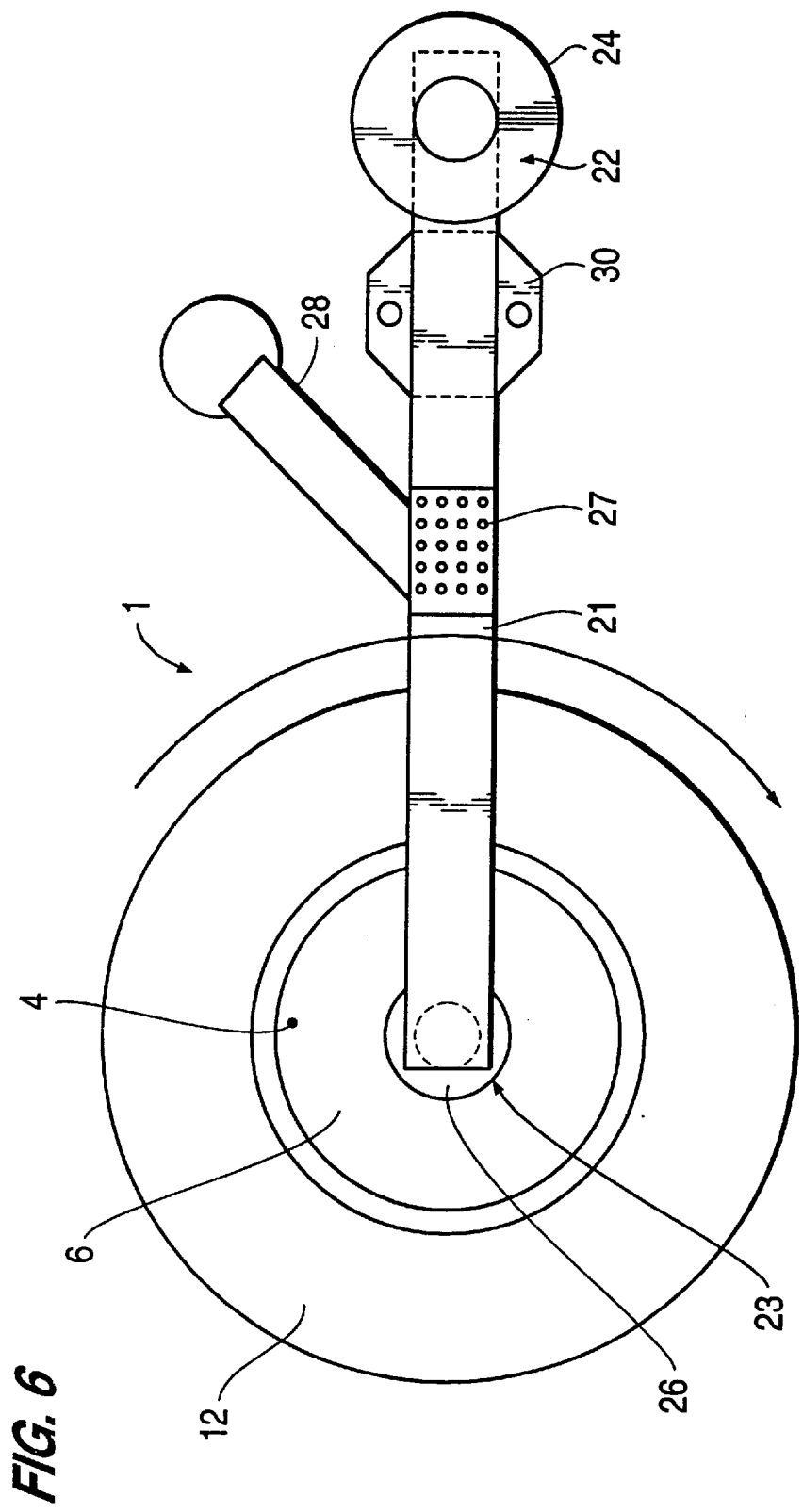
FIG. 6 is a plan view of the inventive apparatus of FIG. 5.

Objects or articles G to be inspected, such as tablets, dragees, film tablets, capsules, etc., are first supplied by means of a (not illustrated) supply mechanism e.g. like that shown in FIG. 6, to the separating device 2. The articles G to be inspected drop via the supply device into the central area of the conical feed section 6 and slide on the cone up to the inlet of the ring slot S and are oriented by the rotary movement in such a way that they rest flat on the conical feed section 6, i.e. with their height perpendicular to the face of the conical section 6, so that they can in this way slide with a horizontally oriented height into the ring slot S. In addition, a member is provided for breaking up an accumulation of the articles arriving at the slot S and in the represented embodiment it is constituted by a brush 123.

In the ring slot S the articles G accumulate in the oriented manner and are individually received by the grooves or shafts 11 in the form of a linear row. If one of the grooves or shafts 11, during the rotation of the separating body 4, passes into the transfer area with respect to the support 102, the lamellar spring 32 is raised to such an extent by the stationary magnet 36*a* that the grooves or shafts 11 are freed at the bottom and an article G can slide out downwards. The spring 32 is supported on the cover 10. A dropping out of the articles G is prevented by a bypass means 13 arranged in stationary manner only in the area. The support curve 15 now allows the article G to slide in the groove 11 initially up to completely below the spring 32. During further rotation of the support 102 in the direction indicated by the arrow, as a result of the stationary arrangement of the magnet 36*a*, its action on the spring 32 is eliminated, so that the latter closes the groove or shaft 11 and consequently prevents a further sliding of further articles G. Simultaneously the curve 15 is lowered and consequently permits a further sliding of the separated article G until it comes to rest concentrically or centrally in front of the suction hole 104. During a further rotation in the direction 50 the suction hole 104 reaches the stationary suction channel 106, so that still in the vicinity of the bypass means 13 the article G is subject to suction action by the vacuum exerted by a pump in the suction channel 106 and is consequently secured in this exactly defined position.

As soon as the article G has been moved past the camera system 130, it is illuminated with diffused light by the lighting device 135*a* and is inspected by the camera 134*a* for defects on its outwardly directed top surface. The article G is then conveyed on by the support 102 until it reaches the transfer point 105. At this point the article is suctioned by means of the vacuum exerted in the suction channel 108 through a corresponding suction hole 107 against the latter, the transfer being assisted in that the suction hole 104 leaves the area of the stationary suction channel 106, i.e. the suction action is eliminated and the suction hole 107 reaches the area of the stationary suction channel 108, so that the suction action is correspondingly produced in the direction of the support 103. The vacuum in the suction channel 108 is such that it overcomes any suction forces still present in the suction channel 106 and the gravity of the article G to be inspected, so that the article G is transferred from support 102 to support 103. The article G is then moved past the camera system 131, 132 and 133, it being inspected by the camera system 131 on its bottom side opposite to the top side inspected by the camera system 130 and which is now outwardly directed on the support 103. The camera systems 132 and 133 preferably inspect by means of the mirrors 138*a* and 138*b* the circumferential faces of the articles G.

The video images of the article G produced by the camera systems 131, 132, 133 and 130 are then passed on to the image processing unit, where they are evaluated according to per se known methods. Divergences from the geometrical shape, e.g. due to larger breaks, can be easily detected in this way. For detecting smaller surface defects there is generally a nominal-actual value comparison between produced and stored images. As the articles G to be inspected have notches or embossings and with this respect cannot be separated in positionally accurate manner, here a nominal-actual value comparison would require a mathematical rotation of the video images produced. This in turn increases the calculating effort and expenditure, as well as the time required to a significant extent. Thus, in the apparatus according to the invention evaluation takes place by evaluating the gradient of the grey value change of adjacent image points. Production-caused irregularities of the surface, such as notches or embossings, have relatively shallow gradients and regular paths, whereas defects have "steep" gradients and/or irregular paths, so that in this way it is possible to achieve a reliable inspection in the millisecond range with a correspondingly good resolution.

After inspection has taken place through the camera systems 130–133 the article G passes into the delivery area 40, 41 and 42, where the article G is delivered to one of the channels 44, 46 and 49 in accordance with the inspection result. If, for example, the evaluation has revealed that at least one video image of the article G produced is defective, then the blast nozzle 48 is activated on passing the particular article G and the latter is ejected into the continuation channel 46. The activation signal is maintained until no further faulty article passes the ejecting device 42. If no defect is detected, the blast nozzle 47 is activated on passing a satisfactory article G and the latter passes into the continuation channel 44. Here again the activation signal is maintained for as long as satisfactory articles pass the ejecting device 41. If individual articles G are not ejected due to faults in the ejecting devices 47, 48, they automatically drop into the continuation channel 49, because in this area the suction action for the article G declines, because there the end of the section channel 108 is reached. Articles G ejected in this way into the continuation channel 49 are looked upon as faulty. Thus, the invention provides a self-monitoring or validatable system.

All parts coming into contact with the articles to be inspected can be easily replaced if the apparatus is to be used for inspecting other articles.

The invention permits a separation or individualization of small articles G with a high throughput, because in the separating device 2 all the articles do not have to be lined up in succession in a row and instead separation initially takes place partly in parallel through the plurality of shafts 11 acting as a buffer store or magazine. As a result the rotation speed of the separating body 4 can be kept low, so that there is no need to fear a crushing of sensitive articles, such as tablets, between the separating body 4 and the surrounding torus 12 and through the detachable holding device 32 a planned transfer of the articles G into the suction holes 14 and 104 is possible.

We claim:

1. An apparatus for separating small articles comprising:
    a rotatably mounted separating device which rotates about a vertical axis and having symmetry about the vertical axis, the device having an upper substantially conical feed section and a base extending below the conical feed section;
    an outer section spaced from the base by a dimension at least equal to a thickness of the small articles and surrounding the base, the spacing of the outer section from the base defining a slot through which the small articles pass vertically;
    a part of the base being divided into a plurality of spaced apart individual shafts disposed circumferentially about the base for receiving the small articles from the slot, the shafts having a dimension at least equal to the thickness of the small articles with adjacent shafts being separated by ribs between the shafts disposed circumferentially about the base;
    hold back members associated with the individual shafts, each hold back member selectively blocking passage of the small articles from each shaft when disposed in a first position in the shaft and permitting the articles to pass through the shaft when disposed in second position outside the shaft, the hold back members comprising springs which, without external influence, are positioned in the first position; and
    magnets associated with springs, each spring being selectively magnetically linked with the associated spring, each magnet upon being magnetically linked with the associated spring positioning the associated spring in the second position to permit the small articles to pass through the associated shaft.

2. An apparatus according to claim 1 wherein:
    the outer section comprises a torus surrounding the base.

3. An apparatus according to claim 2 wherein:
    the torus is fixed.

4. An apparatus according to claim 1 wherein:
    the upper substantially conical feed section and the torus forms a funnel in a vicinity of a top of the slot.

5. An apparatus according to claim 1 wherein:
    the outer section is substantially cylindrical.

6. An apparatus according to claim 1 wherein:
    the part of the base divided into spaced apart individual shafts is a lower part of the base and is substantially frustum-shaped.

7. An apparatus according to claim 1 wherein:
    an upper part of the base is substantially cylindrical.

8. An apparatus according to claim 1 further comprising:
    a transfer area adjacent the base having a substantially horizontal surface for receiving the small articles from the individual shafts.

9. An apparatus according to claim 8 wherein:
    the substantially horizontal surface comprises at least one disk having a face with suction holes disposed in a circular path and coupled to a vacuum source for retaining the articles.

10. An apparatus according to claim 9 wherein:
    the suction holes move synchronously with lower ends of the shafts.

11. An apparatus according to claim 10 wherein:
    the shafts and suction holes have an identical circumferential spacing relative to the vertical axis.

12. An apparatus according to claim 1 further comprising:
    a first support for receiving the small articles from the individual;
    a second support for receiving the small articles from the first support; and
    a vacuum source coupled to the first and second supports for holding the articles.

13. An apparatus according to claim 12 wherein:
    the separating device is concentric to and moves synchronously with the first support and is connected to the first support device.

14. An apparatus according to claim 12 further comprising:
    a detector device positioned radially relative to the first support; and
    suction holes coupled to the vacuum source for holding the articles on the first support.

15. An apparatus according to claim 14 wherein:
    the suction holes of the first and second supports are connectable to stationary suction channels which are connectable to the vacuum source.

16. An apparatus according to claim 14 further comprising:
    a bypass with a support curve for correctly positioning a supply of the articles in front of the suction holes of the first support.

17. An apparatus according to claim 12 wherein:
    the first and second supports each comprise suction holes disposed in a circular path in a circumferential wall thereof, circumferential walls of the first and second supports during rotation of the first and second supports pass each other with a spacing exceeding the thickness of the articles, the suction holes facing one another and being oriented in an aligned manner to each other at a transfer point between the first and second supports.

18. An apparatus according to claim 17 further comprising:
    a plurality of detector devices arranged in a vicinity of a path of movement of the suction holes, one detector device being oriented radially relative to and facing the first support, and at least one additional detector device being positioned axially parallel to and facing a path of movement of the suction holes in the second support.

19. An apparatus according to claim 1 further comprising:
    a device for transferring the small articles to the separating device.

20. An apparatus according to claim 19 wherein:
    the device for transferring the small articles transfers the small articles to the upper conical feed section.

21. An apparatus according to claim 19 wherein:
    the device for transferring the small articles is a supply chute.

22. An apparatus according to claim 19 further comprising:

a vibrating drive for vibrating the device for transferring the articles.

23. An apparatus according to claim 19 wherein:

the device for transferring the articles has a screen for separating fragments.

24. An apparatus according to claim 1 wherein:

a bottom article in each shaft is held by the spring associated with the shaft.

25. An apparatus according to claim 1 further comprising:

separating devices disposed in the slots for separating individual small articles in the slots.

* * * * *